US008543211B2

(12) United States Patent
Simon

(10) Patent No.: US 8,543,211 B2
(45) Date of Patent: Sep. 24, 2013

(54) METHODS AND APPARATUS FOR DEEP BRAIN STIMULATION

(75) Inventor: Bruce J. Simon, Mountain Lakes, NJ (US)

(73) Assignee: Electrocore, LLC, Basking Ridge, NJ (US)

( * ) Notice: Subject to any disclaimer, the term of this patent is extended or adjusted under 35 U.S.C. 154(b) by 1092 days.

(21) Appl. No.: 12/507,135

(22) Filed: Jul. 22, 2009

(65) Prior Publication Data

US 2010/0010564 A1    Jan. 14, 2010

Related U.S. Application Data

(63) Continuation-in-part of application No. 12/394,972, filed on Feb. 27, 2009, now Pat. No. 8,401,650, which is a continuation-in-part of application No. 12/338,191, filed on Dec. 18, 2008, now Pat. No. 8,209,034.

(60) Provisional application No. 61/043,802, filed on Apr. 10, 2008, provisional application No. 61/043,805, filed on Apr. 10, 2008.

(51) Int. Cl.
*A61N 1/00*    (2006.01)

(52) U.S. Cl.
USPC .......................................................... 607/45

(58) Field of Classification Search
USPC ................... 607/45, 88, 40, 46; 604/20, 41, 604/45, 48, 100
See application file for complete search history.

(56) References Cited

U.S. PATENT DOCUMENTS

| | | | |
|---|---|---|---|
| 5,540,730 A | 7/1996 | Terry, Jr. et al. | |
| 5,634,899 A * | 6/1997 | Shapland et al. | ............. 604/507 |
| 5,707,400 A | 1/1998 | Terry, Jr. et al. | |
| 5,735,817 A * | 4/1998 | Shantha | ................... 604/100.02 |
| 6,083,249 A | 7/2000 | Familoni | |
| 6,083,255 A | 7/2000 | Laufer et al. | |
| 6,198,970 B1 | 3/2001 | Freed et al. | |
| 6,327,503 B1 | 12/2001 | Familoni | |
| 6,341,236 B1 | 1/2002 | Osorio et al. | |
| 6,347,247 B1 | 2/2002 | Dev et al. | |
| 6,356,786 B1 | 3/2002 | Rezai et al. | |
| 6,356,787 B1 | 3/2002 | Rezai et al. | |
| 6,366,814 B1 | 4/2002 | Boveja et al. | |
| 6,438,423 B1 | 8/2002 | Rezai et al. | |
| 6,609,030 B1 | 8/2003 | Rezai et al. | |
| 6,610,713 B2 | 8/2003 | Tracey | |
| 6,656,960 B2 | 12/2003 | Puskas | |
| 6,778,854 B2 | 8/2004 | Puskas | |
| 6,819,956 B2 | 11/2004 | DiLorenzo | |
| 6,865,416 B2 | 3/2005 | Dev et al. | |
| 6,871,092 B2 | 3/2005 | Piccone | |

(Continued)

*Primary Examiner* — Robert N Wieland
(74) *Attorney, Agent, or Firm* — Dentons US LLP

(57) ABSTRACT

The present invention provides systems, apparatus and methods for treating nerve disorders in the brain. An electrode is introduced into a patient's sinus cavity and an electrical impulse is applied to the electrode to modulate one or more target nerves in the brain to treat the disorder. In preferred embodiments, the electrode is positioned within a sinus cavity adjacent to or near the frontal cortex of the brain and the electrical signal is sufficient to modulate, stimulate and/or inhibit nerves within the frontal cortex. The electrode may be movable between a collapsed or compact configuration for introduction into the sinus cavity and an expanded configuration for contacting tissue within the sinus cavity to deliver the electrical impulse through the tissue to the target nerves in the brain.

6 Claims, 4 Drawing Sheets

(56) References Cited

U.S. PATENT DOCUMENTS

| | | |
|---|---|---|
| 6,885,888 B2 | 4/2005 | Rezai |
| 6,934,583 B2 | 8/2005 | Weinberg et al. |
| 6,937,896 B1 | 8/2005 | Kroll |
| 7,072,720 B2 | 7/2006 | Puskas |
| 7,142,910 B2 | 11/2006 | Puskas |
| 7,292,890 B2 | 11/2007 | Whitehurst et al. |
| 7,310,552 B2 | 12/2007 | Puskas |
| 8,032,222 B2 * | 10/2011 | Loushin et al. ............ 607/40 |
| 2002/0010495 A1 | 1/2002 | Freed et al. |
| 2002/0016344 A1 | 2/2002 | Tracey |
| 2002/0016615 A1 | 2/2002 | Dev |
| 2002/0116030 A1 | 8/2002 | Rezai |
| 2002/0198570 A1 | 12/2002 | Puskas |
| 2003/0074039 A1 | 4/2003 | Puskas |
| 2004/0059383 A1 | 3/2004 | Puskas |
| 2004/0172075 A1 | 9/2004 | Shafer et al. |
| 2004/0249416 A1 | 12/2004 | Yun et al. |
| 2005/0021092 A1 | 1/2005 | Yun et al. |
| 2005/0065553 A1 | 3/2005 | Ben Ezra et al. |
| 2005/0065562 A1 | 3/2005 | Rezai |
| 2005/0065573 A1 | 3/2005 | Rezai |
| 2005/0125044 A1 | 6/2005 | Tracey |
| 2005/0149146 A1 | 7/2005 | Boveja et al. |
| 2005/0153885 A1 | 7/2005 | Yun |
| 2005/0240241 A1 | 10/2005 | Yun |
| 2005/0256028 A1 | 11/2005 | Yun |
| 2006/0135998 A1 | 6/2006 | Libbus et al. |
| 2006/0167498 A1 | 7/2006 | DiLorenzo |
| 2007/0106337 A1 | 5/2007 | Errico et al. |
| 2007/0106338 A1 | 5/2007 | Errico |
| 2007/0106339 A1 | 5/2007 | Errico et al. |
| 2007/0225768 A1 | 9/2007 | Dubak |
| 2008/0027346 A1 * | 1/2008 | Litt et al. ............ 600/544 |
| 2010/0241190 A1 * | 9/2010 | Kilgore et al. ............ 607/48 |
| 2012/0071811 A1 * | 3/2012 | Ansarinia ............ 604/20 |

* cited by examiner

METHODS AND APPARATUS FOR DEEP BRAIN STIMULATION

CROSS REFERENCE TO RELATED APPLICATIONS

The present application is a continuation-in-part of U.S. patent application Ser. No. 12/394,972, filed Feb. 27, 2009, Publication No. 2009-0259274, publication date Oct. 15, 2009, which claims the benefit of provisional patent application Ser. Nos. 61/043,805 and 61/043,802, filed Apr. 10, 2007, and which is a continuation-in-part of U.S. patent application Ser. No. 12/338,191, filed Dec. 18, 2008 now U.S. Pat. No. 8,209,034 issued Jun. 26, 2012, the complete disclosures of which are incorporated herein by reference for all purposes.

BACKGROUND OF THE INVENTION

The present invention relates to the delivery of electrical energy to bodily tissues for therapeutic purposes, and more specifically to devices and methods for treating various disorders resulting from nerve transmissions in the brain.

The use of electrical stimulation for treatment of medical conditions has been well known in the art for nearly two thousand years. Electrical stimulation of the brain and the peripheral nervous system and/or direct stimulation of malfunctioning tissue is generally a completely reversible and non-destructive treatment and holds significant promise for the treatment of many ailments.

Deep brain stimulation (DBS) is a surgical treatment involving the implantation of a medical device called a brain pacemaker, which sends electrical impulses to specific parts of the brain. DBS in select brain regions, such as the frontal cortex, has provided remarkable therapeutic benefits for otherwise treatment-resistant movement and affective disorders, such as chronic pain, Parkinson's disease, obsessive-compulsive disorder, major depression, essential tremor and dystonia. Although the exact principles and mechanisms of DBS are still not clear, DBS apparently changes brain activity directly in a controlled manner.

In addition to currently recognized neural circuits associated with behavioral disorders, there is an increasing awareness that abnormal neural activity in the brain may be associated with a variety of deleterious behavior patterns. For example, while obesity is not uniformly recognized as a class of psychiatric behavioral disorder, there is recent clinical evidence demonstrating that hyperphagia (excessive appetite and consumption of food) can be associated with excessive activity in certain neural circuits.

Deep brain stimulation systems typically consist of three components, the implanted pulse generator (IPG), the lead and the extension. The IPG is a battery-powered neurostimulator encased in a titanium housing, which sends electrical pulses to the brain to interfere with neural activity at the target site. The lead is a coiled wire insulated in polyurethane with four platinum iridium electrodes connected to the IPG by the extension, an insulated wire that runs from the head, down the side of the neck and behind the ear to the IPG. The IPG is typically placed subcutaneously below the clavicle, or in some cases, the abdomen.

DBS leads are placed in the brain according to the type of symptoms to be addressed. For non-Parkinsonian essential tremor, the lead is typically placed in the ventrointermedial nucleus (VIM) of the thalamus. For dystonia and symptoms associated with Parkinson's disease (rigidity, bradykinesia/akinesia and tremor), the lead is typically placed in either the globus pallidus or subthalamic nucleus.

Unfortunately, deep brain stimulation generally involves the invasive placement of electrodes into deep brain structures, along with the subcutaneous implantation of the electrical generator with batteries. Such approaches are expensive and generally accompanied by risks associated with surgery. In particular, implantation of the electrodes have risks associated with surgically accessing tissues of the brain, such as bleeding and infection. In addition, these approaches suffer from device-related risks, including device failure, battery-life limits and the like Deeper areas of the brain are difficult to reach with current DBS techniques without damaging otherwise healthy areas of the brain. A recent improvement over DBS is to stimulate the brain noninvasively. Newer techniques like transcranial magnetic stimulation have attempted to accomplish this and have shown efficacy in treating depression. However, they have not been able to target small regions of the brain and require large, expensive devices to deliver currents sufficient to induce electric fields in the brain capable of depolarizing nerve membranes.

In light of the above, improved systems, devices and methods for the treatment of disorders associated with nerve transmissions in the brain are desired. In particular, it would be desirable if these systems and methods could help mitigate the debilitating effects of behavioral and other disorders without imposing excessive surgical trauma on the patient, and without having to damage or kill healthy neural tissues.

SUMMARY OF THE INVENTION

The present invention provides systems, apparatus and methods for selectively applying electrical energy to body tissue. In one aspect of the invention, a method for treating nerve disorders in the brain includes introducing an electrode into a patient's sinus cavity and applying an electrical impulse to the electrode that is sufficient to modulate one or more target nerves in the brain to treat the disorder. In preferred embodiments, the electrode is positioned within a sinus cavity adjacent to or near the frontal cortex of the brain and the electrical signal is sufficient to modulate, stimulate and/or inhibit nerves within the frontal cortex. The electrode is preferably movable between a collapsed or compact configuration for advancement into the sinus cavity and an expanded configuration for contacting tissue within the sinus cavity to deliver the electrical impulse through said tissue to the target nerves in the brain.

A key advantage of the invention is that deep brain stimulation (DBS) to treat certain nerve disorders can be accomplished minimally invasively, i.e., without requiring direct access to the brain through the patient's skull. In addition, the proximity of the sinus cavities to the frontal cortex allows precise positioning of the electric field to stimulate the appropriate nerve tissue. Thus, deeper areas of the brain can be directly stimulated without damaging otherwise healthy areas of the brain. Nerve disorders that can be treated according to the present invention include epilepsy, Parkinson's disease, depression, eating disorders, Tourette syndrome, obesity, mood disorders, obsessive-compulsive disorders, hyperphagia, addiction, dystonia, essential tremor, chronic pain or any other disorder associated with nerve transmissions in the frontal cortex.

In a preferred method according to the present invention, an expanded enclosure, such as a balloon, is introduced into a sinus cavity and conductive fluid is delivered within the interior of the balloon. Electrical energy is applied to the conductive fluid such that the electrical energy passes through an ion-permeable section of the outer wall of the balloon to the target tissue. In one embodiment, the electrical energy is applied to an electrode positioned within the balloon and surrounded by the conductive fluid. The conductive fluid allows for the passage of electrical energy from the electrode through the fluid and the outer wall of the enclosure for treatment of tissue on or in a patient. In an alternative embodiment, the electrode comprises part or all of the balloon's outer wall and the electrical energy is applied directly to the conductive fluid.

In the preferred embodiment, the electrode does not directly contact the tissue of the sinus cavity, which reduces the potential for collateral tissue damage or necrosis and/or excessive electric fields in the tissue. In addition, the enclosure physically shields the electrode from the patient's tissue which substantially inhibits Faradic products (e.g., $OH^-$, $H_2O_2$) of the electrode from reaching the target site. In this manner, a direct or low frequency current can be applied to the electrode(s) without the danger of such Faradic products reaching excessively high concentrations at the tissue site. In addition, direct or low frequency current can be delivered for a longer period of time and/or at higher power levels than is conventionally considered safe. Faradic products may be minimized in the present invention either by spacing the electrode from the outer wall of the balloon (so that diffusion is the rate limiting step) or by using a buffered conductive solution as the fluid that expands the balloon.

In an alternative embodiment, a method for diagnosing a patient's hearing deficiency is also disclosed. In this method, an electrode is introduced into the sinus cavity of the patient near or adjacent the cochlea, preferably adjacent the voice canal in the nasal cavity. An electrical impulse is then applied to the electrode that is sufficient to replicate electrical signals that would naturally be generated by one or more nerves of a healthy cochlea. The patient is then monitored to determine if he/she is able to process these electrical signals in the brain and "hear" them. This enables the physician to determine if the patient's hearing deficiency originates in the cochlea and consequently whether a cochlear implant would improve the patient's hearing deficit.

Systems according to the present invention include an enclosure, such as a balloon, that is movable from a deflated position for introduction through one of the patient's nostrils into a sinus cavity to an inflated position wherein at least a portion of the outer wall of the balloon contacts target tissue within sinus. The balloon is preferably inflated by introducing an electrically conductive fluid into the balloon. The conductive fluid serves to inflate the balloon to allow the balloon to contact target tissue, and to electrically couple the electrode to the outer wall of the balloon. The material of the balloon is preferably very soft and flexible, e.g., elastic, such that it gently conforms to the surrounding tissue, which allows the electrically energy to be applied uniformly to the target tissue. In addition, one skilled in the art will recognize that this configuration allows the balloon to conform to tissue within the sinus cavity. Another advantage of the invention is that the balloon, in the inflated position, has a larger tissue contact area than the electrode, which allows the device to be applied to a larger tissue treatment area.

In another aspect of the invention, the device includes an introducer for introducing the device to a target location within the patient's nose. The electrode and the balloon are coupled to a distal portion of the introducer. In a preferred embodiment, the electrode is coupled to the introducer such that, when the balloon is inflated, the electrode is substantially centrally located within the interior of the balloon. This configuration ensures that the electrode is spaced sufficiently from the patient's tissue to minimize tissue necrosis and collateral tissue damage. In certain embodiments, the introducer is a tube designed for passage through the patient's nostril to a target location within the sinus cavities, such as the ethmoid, sphenoid or frontal sinus.

In a particularly preferred embodiment, the balloon is formed substantially from an ion-permeable and/or hydrophilic material. As the balloon is filled with a conductive fluid, such as saline, the outer surface of the balloon wets and permits good contact with the surrounding tissue of the patient, which may otherwise be dry. In certain embodiments, the balloon may include one or more sections formed from an ion-permeable material with other sections formed from an electrically insulating material, or the entire wall of the balloon may be formed from such a material. In the former embodiment, the balloon may be constructed to selectively apply electrical energy through certain sections of its outer wall to selectively apply such energy to specific tissue locations on the body. For example, the balloon may be constructed such that the electrical energy is directly focused from the sinus cavity to the target nerve in the brain, thereby avoiding unwanted stimulation of non-target nerves in the nasal cavity and/or brain.

Preferably, electrical properties of the electrode, the fluid, and the material of the balloon are such that a resistance through the electrode, the fluid, and the balloon outer wall is less than about 1,000 Ohms, more preferably less than about 400 Ohms, and preferably less than 200 Ohms. In one embodiment, the return electrode is a return pad located on a surface of the patient's skin, such as the back or hip, and the electrode within the balloon acts as the tissue treatment or active electrode. In this embodiment, an electromagnetic field emanates from the active electrode through the tissue in a substantially radial pattern. In alternative embodiments, the return electrode may be located closer to the active electrode, e.g., within the balloon, coupled to the introducer outside of the balloon or within a second balloon. In these embodiments, the electrical energy will not flow completely through the patient's body, i.e., the current will generally flow from the active electrode through the conductive fluid and the outer wall of the balloon, through the patient's tissue at the target site and to the return electrode.

In one embodiment, the device further includes a vacuum source for aspirating the electrically conductive fluid from the interior of the balloon. The vacuum source may be a positive source of aspiration with an aspiration passage coupled to the interior of the balloon or the device may be designed to simply allow the fluid to evacuate the balloon through the same fluid passage it entered through pressure differential, gravity, or the like. Evacuating the conductive fluid deflates the balloon and allows any excess Faradic products and/or heat to be evacuated from the device. In this manner, the balloon may be periodically evacuated to allow for periodic evacuation of excess Faradic products and heat, which allows for higher power levels and/or longer continuous use of the device in the patient. In some embodiments, the device may be adapted for continuous circulation of the electrically conductive fluid to reduce any build-up of heat or Faradic products and ensure uniform temperatures at the outer surface of the balloon. These embodiments will allow the device to use much higher power levels as the heat generated around the electrode and within the conductive fluid from the higher power levels will be continuously evacuated from the interior of the balloon.

The source of electrical energy is an electrical signal generator that preferably operates to generate an electrical signal having a frequency between about 1 Hz to 10,000 Hz, a pulse duration of between about 10-1000 us, and an amplitude of between about 1-20 volts. The electrical signal may be one or more of: a full or partial sinusoid, a square wave, a rectangular wave, and triangle wave. By way of example, the at least one electrical signal may be of a frequency between about 15 Hz to 35 Hz. Alternatively, the at least one electrical signal may be of a frequency of about 25 Hz. By way of example, the at least one electrical signal may have a pulsed on-time of between about 50 to 1000 microseconds, such as between about 100 to 300 microseconds, or about 200 microseconds. By way of example, the at least one electrical signal may have an amplitude of about 5-15 volts, such as about 12 volts.

Other aspects, features, advantages, etc. will become apparent to one skilled in the art when the description of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited by or to the precise arrangements and instrumentalities shown.

DETAILED DESCRIPTION OF THE PREFERRED EMBODIMENTS

In the present invention, electrical energy is applied to one or more electrodes in the presence of an electrically conductive fluid to deliver an electromagnetic field to a patient. For convenience, the remaining disclosure will be directed specifically to stimulation of the nerves within the frontal cortex and/or the cochlea with a device introduced into one of the sinus cavities of a patient, but it will be appreciated that the systems and methods of the present invention can be applied equally well to other tissues and nerves of the body, including but not limited to parasympathetic nerves, such as the vagus nerve, sympathetic nerves, spinal or cranial nerves, e.g., optic nerve, facial nerves, vestibulocochlear nerves and the like. In addition, the present invention can be applied to treat other ailments, such as asthma, COPD, sepsis, dialytic hypotension, epilepsy, depression or obesity and other procedures including open procedures, intravascular procedures, interventional cardiology procedures, urology, laparoscopy, general surgery, arthroscopy, thoracoscopy or other cardiac procedures, cosmetic surgery, orthopedics, gynecology, otorhinolaryngology, spinal and neurologic procedures, oncology procedures and the like. In particular, the present invention can be used to practice the treatments described in the following commonly assigned patent applications: US Patent Publication Numbers: 2009/0183237, 2008/0009913, 2007/0191902, 2007/0191905, 2007/0106339, 2007/0106338 and 2007/0106337, the full disclosures of which are incorporated herein by reference.

Figure 1A:
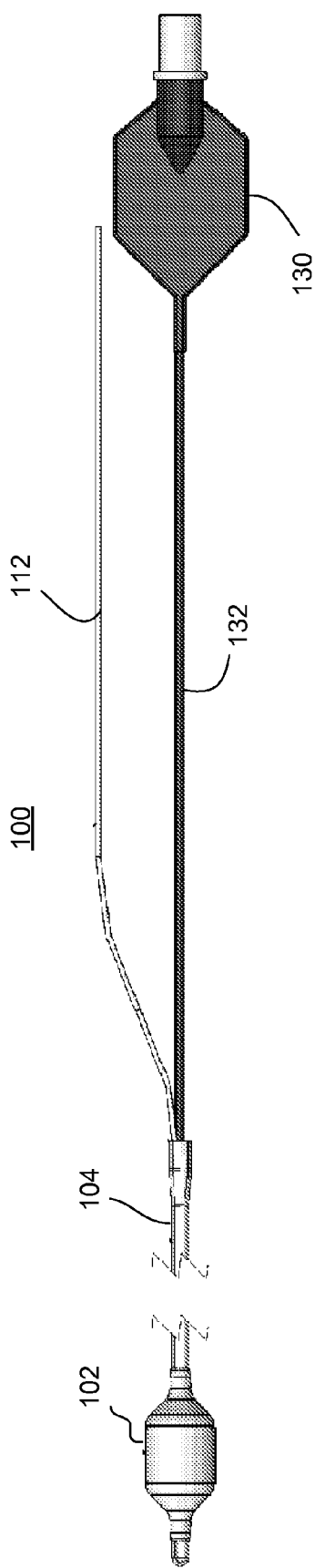
FIG. 1A is a schematic view of an esophageal electrode device in accordance with one or more aspects of the present invention.
Figure 1B:
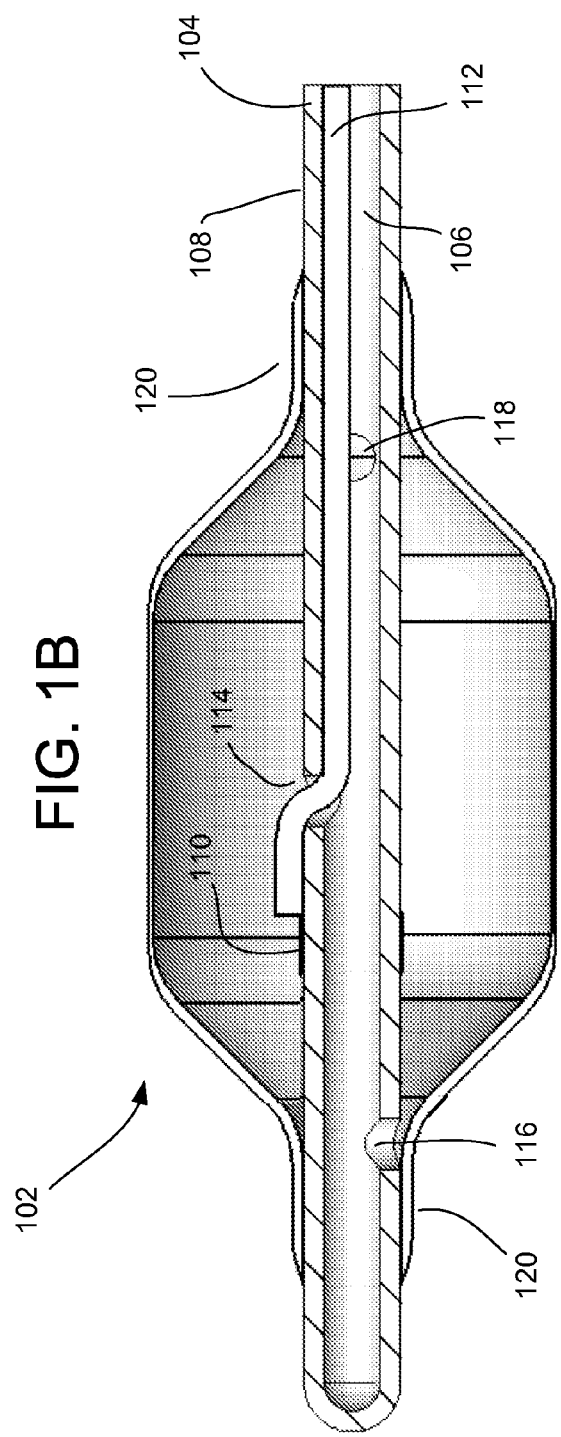
FIG. 1B is a cross-sectional view taken through the balloon of the esophageal electrode device of FIG. 1A.

With reference to FIGS. 1A, 1B, an exemplary device 100 for delivering an electromagnetic field to a patient will now be described. Device 100 is designed to be introduced into the esophagus and/or the sinus cavity of the patient and located therein at a position that (when activated) achieves a therapeutic result. The device 100 includes an inflatable balloon 102 and a catheter, or an introducer tube 104, sized and shaped (when the balloon 102 is deflated) to slide into the patient's esophagus and/or one of the sinus cavities.

The balloon 102 has at least one section formed from an electrically-permeable material, preferably a hydrophilic or ion-permeable material. By way of example, balloon 102 may be substantially formed from an ion-permeable, soft, flexible, and/or distensible material with a thickness of about 0.001 inches. Suitable balloon materials for use in the present invention include Pebax®, aromatic polyether polyurethane grades, such as Dureflex® from, for example, Deerfield Urethane in Whately, Mass., thermally conductive polymers or thermoplastic elastomers (TPE) such as those found at Cool Polymers, Inc. in Warwick, R.I. and the like. However, it will be recognized by those skilled in the art that a variety of commercially available balloon materials may be used to carry out the present invention.

The balloon preferably has a length of between about 1-3 cm (such as 2 cm), a diameter of between about 1.5-4.0 cm (such as 2-3 cm), and a fluid pressure therein of between about 1-10 pounds per square inch (such as 2 psi) when inflated. Obviously, under the stresses experienced during insertion, extraction and inflation, the balloon 102 should not separate from tube 104, tear or leak. The tube 104 may be of a standard type formed out of polyurethane, measuring about 36 cm long, and having inside and outside diameters of 1.6 mm and 2.5 mm, respectively (although other lengths, diameters, and materials may be employed). In order to assist in the placement of the balloon 102 at a desired location, the tube 104 may include markers along its length, such as one marker about every 1 cm.

With reference to FIG. 1B, tube 104 includes an internal passageway 106 and an external surface 108. At least one electrode 110 is coupled to the external surface 108 of the tube 104 (such as by a UV curable adhesive, such as Dymax 204-CTH). By way of example, the at least one electrode 110 may be of a general cylindrical shape and may extend around the external surface 108 of tube 104. Although there are a number of sizes and shapes that would suffice to implement the electrode 110, by way of example, the at least one electrode 110 may be between about 1.0-1.5 mm long (such as 1.27 mm), may have an outside diameter of between about 2.6-2.85 mm (such as 2.77 mm), and may have an inside diameter of between about 2.5-2.75 mm (such as 2.67 mm). A suitable electrode 110 may be formed from Pt—IR (90%/10%), although other materials or combinations or materials may be used, such as platinum, tungsten, gold, copper, palladium, silver or the like.

Those skilled in the art will also recognize that a variety of different shapes and sizes of electrodes may be used. By way of example only, electrode shapes according to the present invention can include ball shapes, twizzle shapes, spring shapes, twisted metal shapes, annular, solid tube shapes or the like. Alternatively, the electrode(s) may comprise a plurality of filaments, rigid or flexible brush electrode(s), coiled electrode(s) or the like. Alternatively, the electrode may be formed by the use of formed wire (e.g., by drawing round wire through a shaping die) to form electrodes with a variety of cross-sectional shapes, such as square, rectangular, L or V shaped, or the like. Alternatively, the electrode may comprise a breakaway electrode on the end of a small gauge needle (e.g., 22 GA). In this embodiment, the electrode is hollow to allow for aspiration through the needle while being inserted ensuring that no blood vessels are compromised. Once in place, the needle is withdrawn over a fine conducting wire which is attached to the electrode, leaving just the electrode near the vagus nerve. The wire is then connected to the negative terminal of source of electrical energy. In yet another embodiment, the syringe itself is the electrode. The needle is coated with a thin insulating material leaving only 1-2 mm of the distal end of the needle bare, which acts as the electrode.

A conductor 112 extends through the internal passageway 106 of tube 104 and electrically connects to the electrode 110. By way of example, the conductor 112 may be a solid silver wire of about 0.25 mm diameter insulated with a PTFE material of about 0.33 mm diameter. The diameter of the insulating material of the conductor 112 should be less than the internal diameter of tube 104 such that fluid may freely flow therein despite the presence of the conductor 112. The conductor 112 may be laser welded to the electrode 110 using known procedures.

Figure 2A:
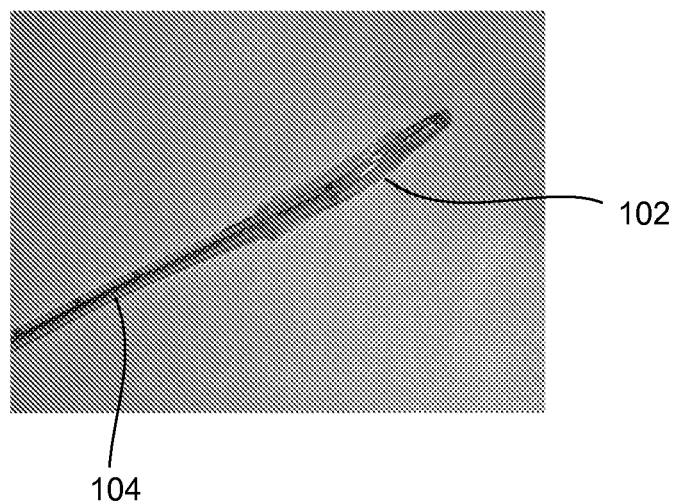
FIG. 2A is an illustration of a deflated balloon of the esophageal electrode device of FIG. 1A.
Figure 2B:
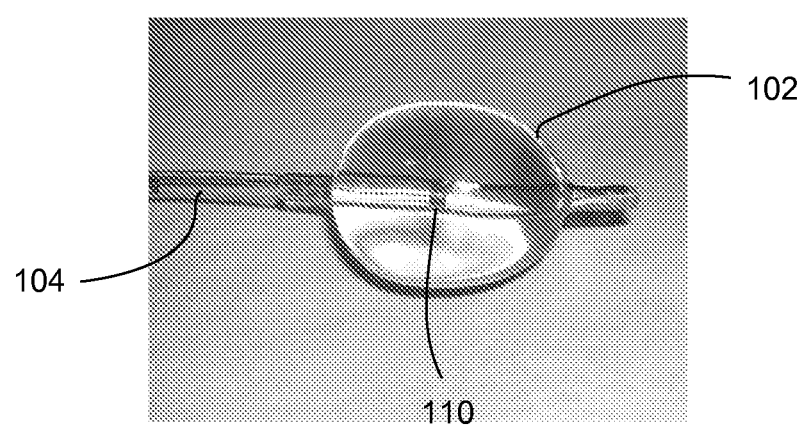
FIG. 2B is an illustration of an inflated balloon of the esophageal electrode device of FIG. 2A.

FIG. 1B is a schematic illustration of the balloon 102 in an inflated state, while FIG. 2B is a reproduction of a photograph illustrating a prototype of the device 100 with the balloon 102 inflated. FIG. 2A is a reproduction of a photograph illustrating the prototype of the device 100 with the balloon 102 deflated. A fluid, preferably a saline solution, passes into the balloon 102 through tube 104 to inflate same. In some embodiments, the fluid may be a buffered conductive solution that will further minimize Faradic products from the electrode contacting the patient's tissue (as discussed below). The balloon 102 is sized, shaped and located about the electrode 110 and a portion of tube 104 such that when the balloon is inflated with fluid, the electrode 110 is substantially centrally located within an interior volume of the balloon 102. This configuration has several advantages over conventional electrode configurations, such as: (i) the metal of the electrode 110 is not too close to, and never comes in contact with, the patient's tissue, which means that there is no concern about tissue necrosis or excessive electric fields in the tissue; (ii) the electrode 110 may be used with direct current signal sources since any Faradic Products (e.g. $OH^-$, $H_2O_2$) would not reach excessively high concentrations at the tissue site; (iii) as the balloon 102 is filled with saline, the surface of the balloon 102 wets and permits good contact with the surrounding tissue of the patient, which may otherwise be dry; and (iv) the material of the balloon 102 is preferably very soft and flexible such that it gently conforms to the surrounding tissue.

To inflate the balloon 102, a number of features are provided with the device 100. A pilot balloon assembly 130, which may be of a standard type, is located at a proximal end of the device 100. The pilot balloon assembly 130 is in fluid communication with tube 104 via fluid tube 132. The fluid tube 132 may enter tube 104 along with the conductor 112, and the entry point may be sealed with an adhesive, such as Dymax 204-CTH UV curable adhesive. The pilot balloon assembly 130 includes a spring loaded valve that opens when introducing fluid into the pilot and the fluid tube 132, and/or when removing fluid therefrom.

Tube 104 may include a first aperture 114 through which the conductor 112 passes from the internal passageway 106 to the at least one electrode 110. The tube 104 may include second and third apertures 116, 118 extending from the internal passageway 106 to the external surface 108, and through which fluid may pass to inflate and deflate the balloon 102 (as will be discussed in more detail later herein). Preferably, the second and third apertures 116, 118 are disposed at proximal and distal ends 120, 122 of the balloon 102, respectively, and the first aperture 114 is located between the second and third apertures 116, 118.

The inflation process preferably includes a priming phase followed by an inflation phase. The priming phase preferably takes place prior to introducing the device 100 into the patient. In the priming phase, a source of fluid, such as saline, is coupled to the pilot balloon assembly 130. The source of fluid may be a fluid filled syringe or the like. With the balloon 102 in a generally vertical orientation (with distal end 120 up), fluid is preferably introduced into the pilot, the fluid tube 132, tube 104 and the balloon 102 via the syringe. The fluid will enter the balloon 102 mostly via the second and third apertures 116, 118. Air will tend to collect at the distal end 120 of the balloon 102 as the fluid enters the device and urges the air in that direction. Again, keeping the balloon upright, at least some of the fluid is drawn out of the balloon 102 by reversing the fluid flow at the pilot balloon assembly 130 and source of fluid. This reversal of fluid flow will create a vacuum and draw all the air out of the balloon 102 via the second aperture 116. Of course, there may be other ways to prime the device 100; however, the above approach is believed to be suitable.

After the device 100 is inserted into the patient's esophagus and/or one of the sinus cavities (preferably through the nostril), the inflation phase begins. The inflation phase includes causing the fluid to flow into the device 100 from the source (e.g., the syringe) until a desired balloon size and/or pressure is reached, such as the aforementioned 1-3 cm length, 1.5-4.0 cm diameter, and/or 1-10 psi pressure.

The electrical properties of the electrode 110, the fluid, and the material of the balloon 102 are preferably designed such that a resistance therethrough is no more than about 1000 Ohms, preferably no more than 500 Ohms and more preferably 200 Ohms or less. In an exemplary embodiment, the impedance through the electrode 110, the fluid, and the material of the balloon 102 should be no more than about 200 Ohms at 1000 Hz. The electrical properties of the fluid may be as important as those of the electrode 110 in this regard. The electrically conducting fluid should have a threshold conductivity to provide a suitable conductive path between electrode 110 and the outer wall of the balloon 102. The electrical conductivity of the fluid (in units of milliSiemans per centimeter or mS/cm) will typically be between about 1 mS/cm and 200 mS/cm and will usually be greater than 10 mS/cm, preferably will be greater than 20 mS/cm and more preferably greater than 50 mS/cm. In one embodiment, the electrically conductive fluid is isotonic saline, which has a conductivity of about 17 mS/cm. Applicant has found that a more conductive fluid, or one with a higher ionic concentration, will usually provide optimal results. For example, a saline solution with higher levels of sodium chloride than conventional saline (which is on the order of about 0.9% sodium chloride) e.g., on the order of greater than 1% or between about 3% and 20%, may be desirable. A fluid of about 5% saline (e.g., approximately 100 mS/cm) is believed to work well, although modifications to the concentration and the chemical make-up of the fluid may be determined through simple experimentation by skilled artisans.

As noted above, the material of the balloon 102 is preferably slightly water-permeable or hydrophilic so that when the balloon 102 is filled with saline, the surface of the balloon 102 wets. Preferably, when filled with 10 cc of saline, the flux of saline out of the balloon 102 (into a similar saline solution) should not exceed about 1 cc per hour. Lubrizol Tecophilic HP93A-100 is a material with these properties.

In an alternative embodiment, the electrode 110 may be implemented via the fluid itself within the balloon 102. Although a 5% saline solution would have a relatively high resistance compared to a metal electrode 110 implementation, those skilled in the art would appreciate that higher conductivity fluid solutions may be employed for such purposes or a larger diameter and/or shorter tube may be utilized to increase the conductivity. Additionally or alternatively, the conductor 112 may be implemented using the conductive fluid used to fill the balloon 102; indeed, such fluid is within the passage 106 anyway. Again, relatively high conductivity fluid would be desirable.

Figure 3:
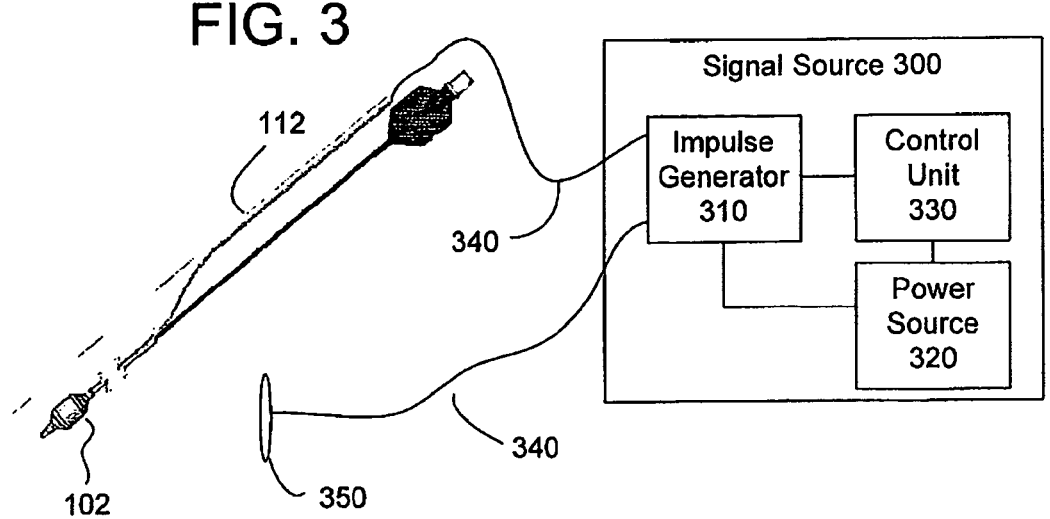
FIG. 3 is a schematic diagram of an electrical signal generating system for use with the esophageal electrode device of FIG. 1A.

With reference to FIG. 3, a complete system for using the device 100 includes an electrical signal generator (or source) 300. Source 300 operates to apply at least one electrical signal to the conductor 112 (via lead 340) such that, when the inflated balloon 102 (and electrode 110) is positioned at the target region within a patient, an electro-magnetic field emanates from the electrode 110 to the anatomy of the patient in the vicinity of the target region to achieve a therapeutic result. Unlike some known techniques, which target a specific location of the patient's anatomy, such as a very specific location of a nerve, the return electrode 350 placement is preferably such that when applied to the patient, the electro-magnetic field emanating from the electrode 110 is a substantially radial pattern—in other words, the pattern of the electromagnetic field emanating from the electrode 110 is not focused on any particular point, or small, localized region of the patient's anatomy. This is preferably achieved by applying the return electrode 350 to an external portion of the patient, such as to at least one of the upper-back, the chest, and/or the stomach.

The source 300 may be tailored for the treatment of a particular ailment and may include an electrical impulse generator 310, a power source 320 coupled to the electrical impulse generator 310, and a control unit 330 in communication with the electrical impulse generator 310 and the power source 320. Electrodes 340 provide source and return paths for the at least one electrical signal to/from the electrode 110 and return electrode 350.

The control unit 330 may control the electrical impulse generator 310 for generation of the signal suitable for amelioration of the ailment when the signal is applied via the electrodes 340 to the device 100. It is noted that source 300 may be referred to by its function as a pulse generator.

Figure 4:
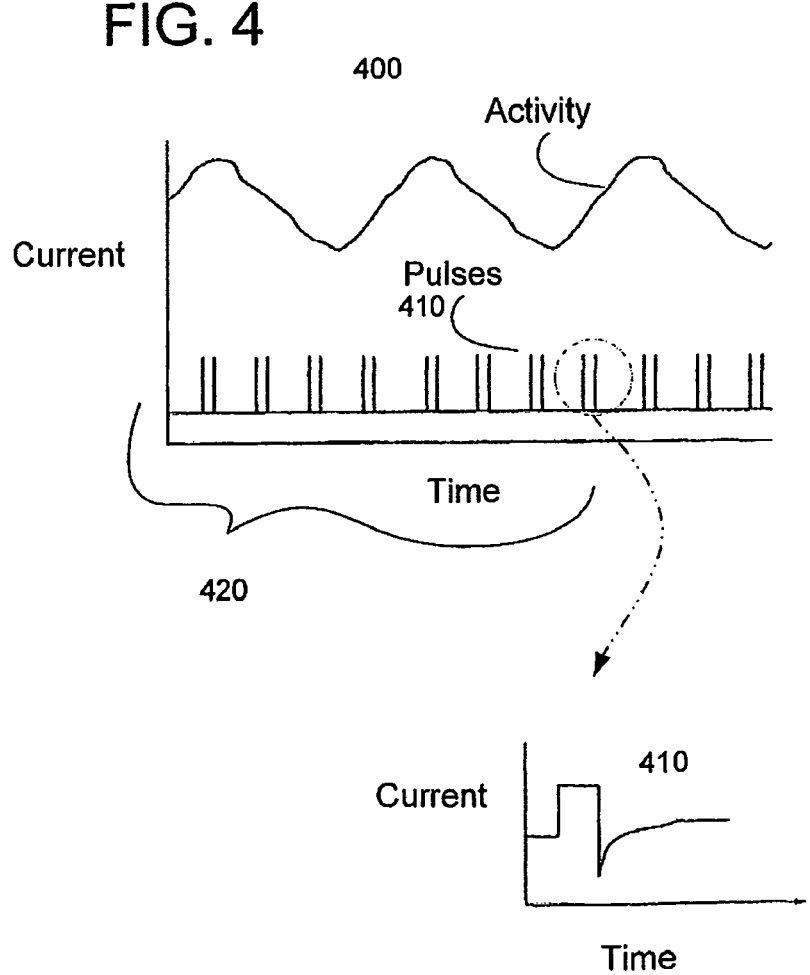
FIG. 4 illustrates an exemplary electrical voltage-current profile for a blocking and/or modulating impulse in accordance with an embodiment of the present invention.

FIG. 4 illustrates an exemplary electrical voltage/current profile for a stimulating, blocking and/or modulating impulse applied to a portion or portions of the patient's anatomy, in accordance with one or more embodiments of the present invention. A suitable electrical voltage/current profile 400 for the stimulating, blocking and/or modulating impulse 410 to the portion or portions of one or more nerves and/or muscles may be achieved using the pulse generator 310. In a preferred embodiment, the pulse generator 310 may be implemented using the power source 320 and control unit 330 having, for instance, a processor, a clock, a memory, etc., to produce a pulse train 420 to the electrode(s) 340 that deliver the blocking and/or modulating fields to the nerve resulting from impulses 410.

The parameters of the modulation signal 400 are preferably programmable, such as the frequency, amplitude, duty cycle, pulse width, pulse shape, etc. The blocking and/or modulating impulse signal 410 preferably has a frequency, an amplitude, a duty cycle, a pulse width, a pulse shape, etc. selected to influence the therapeutic result, such as stimulating, blocking and/or modulating some or all of one or more nerve transmissions.

For example, assuming the aforementioned impedance characteristics of the device 100, the at least one electrical signal may be of a frequency between about 1 Hz to 3000 Hz, a pulse duration of between about 10-1000 us, and an amplitude of between about 1-20 volts. For example, the at least one electrical signal may be of a frequency between about 15 Hz to 35 Hz, such as about 25 Hz. The at least one electrical signal may have a pulsed on-time of between about 50 to 1000 microseconds, such as between about 100 to 300 microseconds, such as about 200 microseconds. The at least one electrical signal may have an amplitude of about 5-15 volts, such as about 12 volts. The at least one electrical signal may include one or more of a full or partial sinusoid, a square wave, a rectangular wave, and triangle wave.

Although the specific implementation of the signal source 300 is not of criticality to the invention, by way of example, the source 300 may be purchased commercially, such as a Model 7432 available from Medtronic, Inc. Alternatively, U.S. Patent Application Publications 2005/0075701 and 2005/0075702, both to Shafer, both of which are incorporated herein by reference, contain descriptions of pulse generators that may be applicable for implementing the signal source 300 of the present invention.

An alternative implementation for the signal source 300 of the present invention may be obtained from the disclosure of U.S. Patent Publication No.: 2005/0216062, the entire disclosure of which is incorporated herein by reference. U.S. Patent Publication No.: 2005/0216062 discloses a multi-functional electrical stimulation (ES) system adapted to yield output signals for effecting faradic, electromagnetic or other forms of electrical stimulation for a broad spectrum of different biological and biomedical applications. The system includes an ES signal stage having a selector coupled to a plurality of different signal generators, each producing a signal having a distinct shape such as a sine, a square or saw-tooth wave, or simple or complex pulse, the parameters of which are adjustable in regard to amplitude, duration, repetition rate and other variables. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type he wishes and the user can then observe the effect of this signal on a substance being treated.

In a preferred embodiment, an electrode is introduced into one of the sinus cavities of a patient to treat nerve disorders in the brain and/or to evaluate hearing deficiencies. In preferred embodiments for treating nerve disorders, the electrode is positioned within a sinus cavity adjacent to or near the frontal cortex of the brain and the electrical signal is sufficient to modulate, stimulate and/or inhibit nerves within the frontal cortex. The electrode is preferably movable between a collapsed or compact configuration for introduction through one of the nostrils into the target sinus cavity and an expanded configuration for contacting tissue within the sinus cavity to deliver the electrical impulse through said tissue to the target nerves in the brain.

A key advantage of the invention is that deep brain stimulation (DBS) to treat certain nerve disorders can be accomplished minimally invasively, i.e., without requiring direct access to the brain through the patient's skull. In addition, the proximity of the sinus cavities to the frontal cortex allows precise positioning of the electric field to stimulate the appropriate nerve tissue. Thus, deeper areas of the brain can be directly stimulated without damaging otherwise healthy areas of the brain. Nerve disorders that can be treated according to the present invention include epilepsy, Parkinson's disease, depression, eating disorders, Tourette syndrome, obesity, mood disorders, obsessive-compulsive disorders, hyperphagia, addiction, dystonia, essential tremor, chronic pain or any other disorder associated with nerve transmissions in the frontal cortex.

One example of a nerve disorder that can be treated according to the present invention is Parkinson's disease. Parkinson's disease is a neurodegenerative disease whose primary symptoms are tremor, rigidity, bradykinesia and postural instability. Deep brain stimulation can be used to control or mitigate the symptoms of Parkinson's disease by sending high frequency electrical impulses into specific areas of the brain. Traditionally, the two most common target sites for nerve stimulation are the subthalamic nucleus (STN) and the globus pallidus internal (GPi), but other sites such as the caudal zona incerta and the pallidofugal fibers medial to the STN, are being evaluated and show promise.

Another example of a nerve disorder that can be treated according to the present invention is major depression. Researchers have shown that electrical stimulation of a small area of the frontal cortex, the subgenual cingulated region, can bring about sustained remissions in patients suffering from major depression. In addition, the nucleus accumbens, the region associated with pleasure and reward mechanisms, has shown promising results with patients suffering from profound depression.

Figure 5:
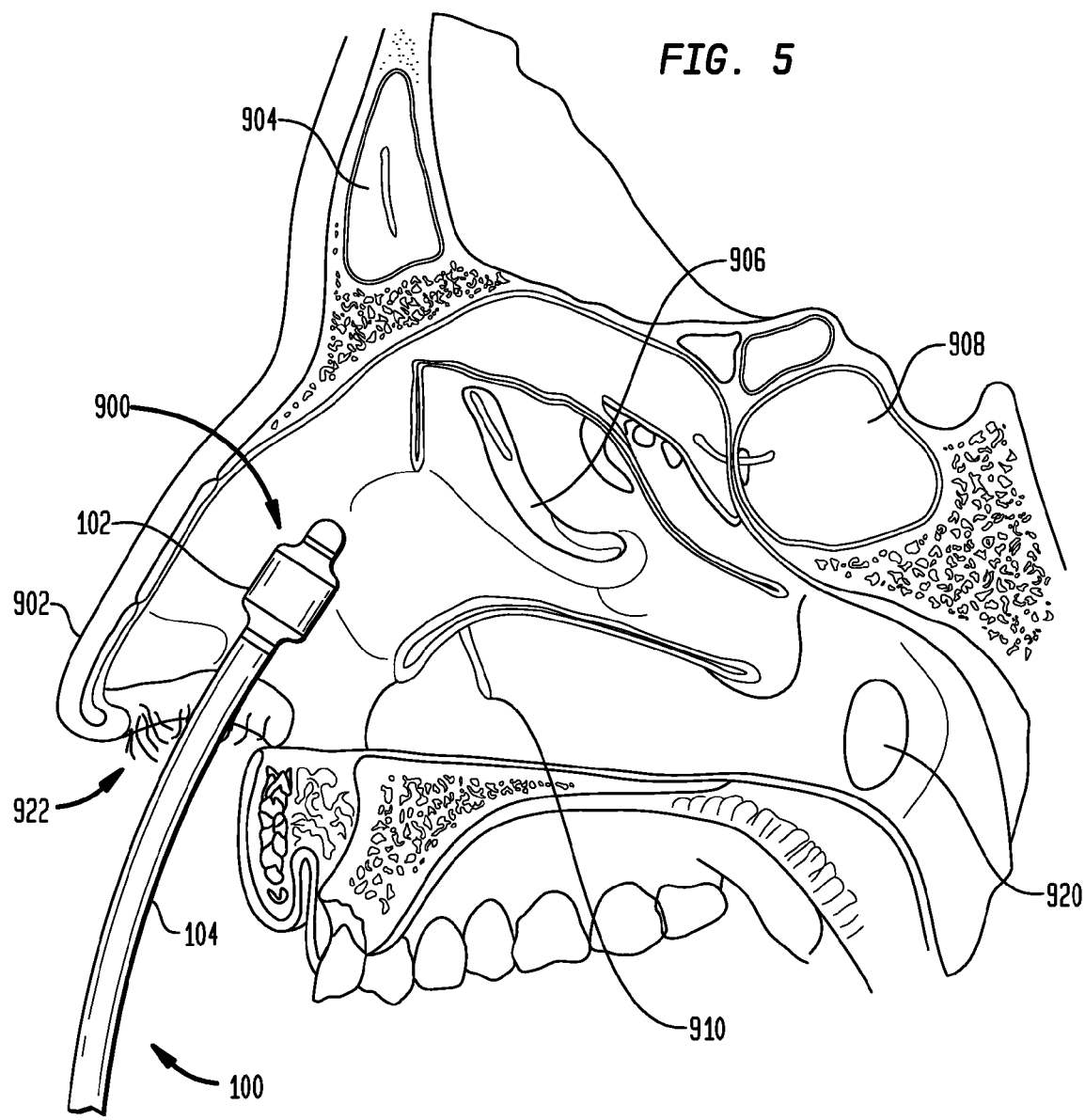
FIG. 5 illustrates a method of treating nerve disorders in the brain according to the present invention.

As shown in FIG. 5, the nasal cavity 900 is a large air-filled space above and behind the nose 902 in the middle of the face. The paranasal sinuses (maxillary, frontal, ethmoid and sphenoid) are air-filled spaces within the bones of the skull and face that communicate with the nasal cavity via small openings or ostia. The frontal sinuses 904 are superior to the eyes in the frontal bone which forms the hard part of the forehead. The maxillary sinuses (only the opening 910 of the maxillary sinus is shown FIG. 5) are under the eyes in the maxillary bone. The ethmoid sinuses 906 are formed from several discrete air cells within the ethmoid bone between the nose and eyes. Finally, the sphenoid sinuses 908 are located in the sphenoid bone at the center of the skull base under the pituitary gland.

In use, an electrode is introduced through the nostril 922 of the patient and advanced into one of the sinus cavities such as the front sinus 904 or the sphenoid sinus 908. In a preferred embodiment, the electrode may be a balloon-electrode device 100 similar to the one shown in FIGS. 1-3 or any suitable electrode device that can be used in the method described below. For example, an expandable electrode may be used that is designed for insertion through the nostril 922 and then for expansion into a large configuration at the target site within the sinus cavities. Alternatively, any standard bipolar or monopolar electrode suitable for delivering the appropriate electrical impulse from the sinus cavities to the target location in the brain may be used to practice the method of the present invention.

The exact location of placement of the electrode(s) will depend on the targeted region of the patient's frontal cortex according to the desired treatment of the nerve disorder. Once in position, a fluid, preferably a saline and/or a buffered conductive solution, passes into balloon 102 through an introducer tube 104 such that when balloon 102 is inflated, electrode 110 (not shown in FIG. 5) is substantially centrally located within the interior of balloon 102. An electrical impulse is then applied to electrode 110 by a suitable impulse generator 310 (FIG. 3) such that the electrical impulse passes through the conductive fluid and the outer surface of balloon 102 into the tissue of the sinus cavity and to the targeted nerve in the patient's brain. The electrical signal may be of a frequency between about 1-3000 Hz, pulse duration between about 10-1000 us, and an amplitude between about 1-20 volts. The exact amplitude will largely depend on the distance between the electrode 110 and the targeted nerve.

The electrical signal is preferably selected to substantially block the nerve signals that cause the disorder to be treated. For example, if the physician is treating non-Parkinsonian essential tremor, the placement of balloon 102 and the amplitude of the signal will both be selected to apply a suitable electrical impulse to block nerves signals emanating from the ventrointermedial nucleus of the thalamus. If the physician is treating dystonia and symptoms associated with Parkinson's disease (rigidity, bradykinesia/akinesia and/or tremor), the balloon 102 is placed and the amplitude is selected to apply the electrical impulse to block nerve signals emanating from either the globus pallidus or subthalamic nucleus.

Balloon-electrode device 100 may be introduced into the sinus cavities for multiple treatments, depending on the nerve disorder. Alternatively, the device may be implanted in one of the sinus cavities. In this embodiment, balloon 102 is detachable from introducer tube 104. In one embodiment, tube 104 includes a one-way valve along its length proximal to balloon 102 such that conductive fluid can be delivered to the interior of the balloon 102 without passing back through tube 104 when the distal portion of tube 104 is detached from balloon 102. When it is desired to apply the electrical impulse, tube 104 may be reattached to balloon 102 to deliver sufficient conductive fluid to expand balloon 102. A wireless transmitter outside of the patient's body may be used to apply the electrical impulse to electrode 110.

In another embodiment, an electrode, such as balloon electrode device 100, may be used to evaluate a patient's hearing deficiency, such as a deficiency related to the cochlea. The cochlea is a spiraled hollow conical chamber of bone that functions as the auditory portion of the inner ear. It is filled with a water liquid, which moves in response to the vibrations coming from the middle ear via the oval window. As the fluid moves, thousands of "hair cells" are set in motion, and this motion is converted into electrical signals that are communicated via neurotransmitters to many thousands of nerve cells. These primary auditory neurons transform the signals into electrical impulses known as action potentials, which travel along the auditory nerve to structures in the brainstem for further processing.

A cochlear implant is a surgically implanted electronic device that provides a sense of sound to a person who is profoundly deaf or severely hard of hearing. The cochlear implant is often referred to as a bionic ear. Unlike hearing aids, the cochlear implant does not amplify sound, but works by directly stimulating any functioning auditory nerves inside the cochlea with an electric field. External components of the cochlear implant may include a microphone, speech processor and an RF transducer or primary headpiece coil. A secondary coil is implanted beneath the skull's skin and inductively coupled to the primary headpiece coil. The headpiece coil has a magnet by which it attaches to another magnet placed on the secondary coil often beside the cochlear implant. The implant relays the incoming signal to the implanted electrodes in the cochlea. The speech processor allows an individual to adjust the sensitivity of the device. The implant gives recipients additional auditory information including sound discrimination fine enough to understand speech in quiet environments.

A cochlear implant will not cure deafness or hearing impairment, but is a prosthetic substitute for hearing. Some recipients find them very effective, others somewhat effective and some feel worse overall with the implant than without. For people already functional in spoken language who lose their hearing, cochlear implants can be a great help in restoring functional comprehension of speech, especially if they have only lost their hearing for a short time. However, some effects of implantation are irreversible; while the device promises to provide new sound information for a recipient, the implantation process inevitably results in damage to nerve cells within the cochlea, which often results in a permanent loss of most residual natural hearing. While recent improvements in implant technology, and implantation techniques, promise to minimize such damage, the risk and extent of damage still varies. Thus, it is important to accurately assess the potential effectiveness of a cochlea implant prior to surgery (to the extent possible).

The present invention provides a system and method of stimulating auditory nerves within the cochlea to determine which nerves are functional and thereby diagnose the patient's hearing deficiency. This allows the physician to more accurately assess the potential effectiveness of a cochlea implant prior to implantation. In a preferred embodiment, balloon 102 is introduced through one of the nostrils 922 of the patient and into a sinus cavity adjacent the pharyngeal orifice 920 of the auditory tube (see FIG. 5). Once in position, a fluid such as isotonic saline passes into balloon 102 through an introducer tube 104 such that when balloon 102 is inflated, electrode 110 is substantially centrally located within the interior of balloon 102. An electrical impulse is then applied to electrode 110 by a suitable impulse generator 310 such that the electrical impulse passes through the conductive fluid and the outer surface of balloon 102 into the tissue of the sinus cavity and to the targeted auditory nerve(s) in the patient's cochlea (not shown).

In this embodiment, the electrical signal(s) will preferably be selected to mimic one or more electrical signals that would be produced by a functioning cochlea. The patient's response to these signals is then monitored to determine whether a cochlea implant would be effective. The electrical signals may be of a frequency between about 1-10,000 Hz, pulse duration between about 10-1000 us, and an amplitude between about 1-20 volts.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for monitoring a patient's hearing comprising:
   introducing an electrode into a sinus cavity in a patient adjacent or near a cochlea; and
   applying an electrical impulse to the electrode sufficient to stimulate one or more auditory nerves in the cochlea.

2. The method of claim 1 further comprising monitoring the patient to determine if the patient can hear the electrical signals produced by the auditory nerves in response to the electrical impulse.

3. The method of claim 1 wherein the introducing step is carried out by advancing the electrode through a nostril of the patient and then expanding the electrode within the sinus cavity.

4. The method of claim 1 wherein the sinus cavity is one of the frontal sinus, the sphenoidal sinus or the ethmoid sinus.

5. The method of claim 1 wherein the introducing step comprises advancing a balloon through a nostril of the patient and expanding the balloon within the sinus cavity.

6. The method of claim 5 wherein the electrode is housed within the balloon, the expanding step being carried out by delivering electrically conductive fluid into an interior of the balloon.

* * * * *